(12) United States Patent
Manalis (10) Patent No.: US 7,387,889 B2
(45) Date of Patent: Jun. 17, 2008

(54) MEASUREMENT OF CONCENTRATIONS AND BINDING ENERGETICS

(75) Inventor: Scott Manalis, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 346 days.

(21) Appl. No.: 10/336,549

(22) Filed: Jan. 2, 2003

(65) Prior Publication Data
US 2004/0038426 A1 Feb. 26, 2004

Related U.S. Application Data

(60) Provisional application No. 60/405,184, filed on Aug. 22, 2002.

(51) Int. Cl.
C12M 1/34 (2006.01)
C12M 1/00 (2006.01)
G01N 25/00 (2006.01)
G01N 21/00 (2006.01)
G01N 33/53 (2006.01)

(52) U.S. Cl. .................. 435/287.1; 436/147; 436/501; 436/164; 435/7.1; 435/283.1; 422/51; 422/68.1

(58) Field of Classification Search ................ 436/807, 436/518, 535; 435/7.1, 182, 286.1, 286.5, 435/287.1; 422/51, 68.1
See application file for complete search history.

(56) References Cited

U.S. PATENT DOCUMENTS 5,156,810 A * 10/1992 Ribi ........................ 422/82.01
6,096,559 A * 8/2000 Thundat et al. ............. 436/147
6,436,647 B1 * 8/2002 Quate et al. .................... 435/6
6,477,901 B1 11/2002 Tadigadapa et al.
6,647,778 B2 * 11/2003 Sparks ..................... 73/204.26
6,846,638 B2 * 1/2005 Shipwash .................... 435/7.1
6,926,864 B2 * 8/2005 Peeters et al. .............. 422/68.1
2002/0015952 A1 * 2/2002 Anderson et al. .............. 435/6
2003/0054355 A1 * 3/2003 Warthoe ......................... 435/6
2003/0057391 A1 * 3/2003 Krulevitch et al. ........... 251/11
2003/0087290 A1 * 5/2003 Tarlov et al. ................... 435/6
2003/0211992 A1 * 11/2003 Chen et al. .................... 514/12

OTHER PUBLICATIONS

McKendry et al. ("Multiple Label-Free Biodetection and Quantitative DNA-Binding Assays on a Nanomechanical Cantilever Array" (2002) Proc Natl Acad Sci 99:9783-9788).*

Fagerstam et al. "Biospecific interaction analysis using surface plasmon resonance detection applied to kinetic, binding site and concentration analysis" Journal of Chromatography 597 (1992) 397-410.*

Ozawa et al. "Metal ion selectivity for formation of the calmodulin-metal-target peptide ternary complex studied by surface plasmon resonance spectroscopy" Biochimica et Biophysica Acta 1434 (1999) 211-220.*

(Continued)

Primary Examiner—Long V. Le
Assistant Examiner—Christine Foster
(74) Attorney, Agent, or Firm—Norma E. Henderson (57) ABSTRACT

Free-standing microfluidic channels are used to both transport and analyze molecules of interest. In a biochemical context, such molecules may be polypeptides, nucleic acids, or other biomolecules. The free-standing channels provide a real-time readout of concentration without the need for labeling with reporter molecules. The channels can also measure enthalpy values and equilibrium constants by detecting heat released from or absorbed by the sample.

11 Claims, 5 Drawing Sheets

OTHER PUBLICATIONS

Yang et al. "Surface effects and high quality factors in ultrathin single-crystal silicon cantilevers," Applied Physics Letters, vol. 77, No. 23, Dec. 4, 2000, pp. 3860-3862.

Yang et al. "Mechanical behavior of ultrathin microcantilever," Sensors and Actuators, 82 (2000), pp. 102-107.

Lo et al. "Organic and Inorganic Contamination on Commercial AFM Cantilevers," Langmuir, vol. 15, No. 19, Mar. 30, 1999, pp. 6522-6526.

Shih et al. "Simultaneous liquid viscosity and density determination with piezoelectric unimorph cantilevers," Journal of Applied Physics, vol. 89, No. 2, Jan. 13, 2001, pp. 1497-1505.

O'Sullivan et al. "Commercial quartz crystal microbalances—theory and applications," Biosensors & Bioelectronics, 14, 1999, pp. 663-670.

Jenkins et al. "Arrays for protein expression profilings: Towards a viable alternative to two-dimensional gel electrophoresis?" Proteomics, 1, 2000, pp. 13-29.

Ma et al. "Brownian Fluctuation Spectroscopy Using Atomic Force Microscopes," Langmuir, 16, 2000, pp. 2254-2261.

Battiston et al. "A chemical sensor based on a microfabricated cantilever array with simultaneous resonance-frequency and bending readout," Sensors and Actuators, B 77 (2001), pp. 122-131.

Westberg et al. "A CMOS-compatible device for fluid density measurements fabricated by sacrificial aluminum etching," Sensors and Actuators, 73 (1999), pp. 243-251.

Vermeer et al. "The Thermal Stability of Immunoglobulin: Unfolding and Aggregation of a Multi-Domain Protein," Biophysical Journal, vol. 78, Jan. 2000, pp. 394-404.

Vanhooren et al. "Structural Basis for difference in Heat Capacity Increments for $Ca^{2+}$ Binding to Two $\alpha$-Lactalbumins," Biophysical Journal, vol. 82, Jan. 2002, pp. 407-417.

Tsodikov et al. "Analytic Binding Isotherms Describing Competitive Interactions of a Protein Ligand with Specific and Nonspecific Sites on the Same DNA Oligomer," Biophysical Journal, vol. 81, Oct. 2001, pp. 1960-1969.

Vermeer et al. "The Unfolding/Denaturation of Immunogammaglobulin of Isotype 2b and its $F_{ab}$ and $F_c$ Fragments," Biophysical Journal, vol. 79, Oct. 2000, pp. 2150-2154.

Moulin et al. "Micromechanical thermal sensor: Comparison of experimental results and simulations," J. Vac. Sci. Technol. B., 15(3), May/Jun. 1997, pp. 590-596.

Jelesarov et al. "Isothermal titration calorimetry and differential scanning calorimetry as complementary tools to investigate the energetics of biomolecular recognition," J. Mol. Recognit., 12:3-18, 1999.

Thibblin et al. "Microcalorimetry as a tool in mechanistic studies of organic reactions," J. Phys. Org. Chem., 15, 2002, pp. 233-241.

Barnes et al. "A femtojoule calorimeter using micromechanical sensors," Rev. Sci. Instrum., 65 (12), Dec. 1994, pp. 3793-3798.

Schreiber. "Kinetic studies of protein-protein interactions," Current Opinion in Structural Biology, 12: 41-47, 2002.

Lakey et al. "Measuring protein-protein interactions," Current Opinion in Structural Biology, 8:119-123, 1998.

Tsai et al. "Transient Thermal Bubble Formation on Polysilicon Micro-Resisters," Journal of Heat Transfer, vol. 124, Apr. 2002, pp. 375-382.

Nakagawa et al. "Picojoule and submillisecond calorimetry with micromechanical probes," Applied Physics Letters, vol. 73, No. 16, Oct. 19, 1998, pp. 2296-2298.

Berger et al. "Thermal analysis using a micromechanical calorimeter," Appl. Phys. Lett. 69 (1), Jul. 1, 1996, pp. 40-42.

Johannessen et al. "Heat conduction nanocalorimeter for pi-scale single cell measurements," Applied Physics Letters, vol. 80, No. 11, Mar. 18, 2002, pp. 2029-2031.

Lin et al. "Microbubble Powered Actuator," Int. Conference on Sensors and Actuators, Transducers 91, Technical Digest, San Francisco, U.S.A. Jun. 1991, pp. 1041-1044.

Tsai et al. "Micro-to-macro fluidic interconnectors with an integrated polymer sealant," J. Micromech. Microeng., 11 (2001) pp. 577-581.

Lin et al. "Silicon-Processed Microneedles," IEEE Journal of Microelectromechanical Systems, vol. 8, No. 1, Mar. 1999, pp. 78-84.

Fritz et al. "Translating Biomolecular Recognition into Nanomechanics," Science, vol. 288, Apr. 14, 2000, pp. 316-318.

* cited by examiner

SAMPLE IS TRANSPORTED INTO U-CHANNEL

FIG. 3A

SAMPLE BINDS TO IMMOBILIZED RECEPTORS

FIG. 3B

SAMPLE IS TRANSPORTED OUT OF U-CHANNEL

MEASUREMENT OF CONCENTRATIONS AND BINDING ENERGETICS

RELATED APPLICATION

This application claims the benefits of and priority to U.S. Provisional Application Ser. No. 60/405,184, filed on Aug. 22, 2002, the entire disclosure of which is hereby incorporated by reference.

BACKGROUND OF THE INVENTION

1. Field of the Invention

The present invention relates to measuring analyte concentrations and the affinity and energetics of chemical binding.

2. Background Information

Analytical study of molecular interactions requires the ability to observe changing molecular concentrations in an environment of interest, and also the ability to quantify chemical kinetics and affinity energetics. This is particularly true in biological contexts, where processes at the cellular and even organismic level often can be traced to changing concentrations and/or binding energetics of biomolecules and cofactors. For example, proteins and their byproducts play a critical role in nearly every event that take place within living cells. The ability to characterize these events is furthered by the ability to profile the concentration of specific proteins as a function of time and various physiological conditions, and the ability to measure the affinity and energetics of protein binding reactions. The rate at which these parameters are measured by current methodology, however, is often limited by requirements for large sample volumes and time-consuming modifications of the molecules under investigation.

For example, relative biomolecular concentration is frequently assayed using two-dimensional gel electrophoresis, a procedure that is time-consuming, labor-intensive, and which requires significant technical expertise to obtain quantitative information. One approach toward circumventing these limitations is to develop the equivalent of a DNA microarray for biomolecules such as proteins. A representative system utilizing this approach involves an antibody array sensitive to the amounts and modification states of endogenous ErbB receptor tyrosine kinases. The array has been employed to monitor the kinetics of signal transduction in human tumor cell lines in a multiplexed fashion. See, e.g., Jenkins et al., "Arrays for protein expression profiling: Towards a viable alternative to two-dimensional gel electrophoresis?", *Proteomics* 1:13-29 (2001).

One requirement for protein arrays that currently limits their widespread use is the need to label sample proteins with a fluorescent marker. Although the labeling process is straightforward for DNA, the complexity of a protein's structure poses significant challenges to attaching labels to specific sites while preserving the functionality of the protein molecule. The development of label-free protein detectors that are scalable for array applications is ongoing. Although approaches such as the quartz crystal microbalance (QCM) and surface plasmon resonance (SPR) can detect label-free binding, they are difficult to miniaturize for protein arrays. See, e.g., O'Sullivan et al., "Commercial quartz crystal microbalances—theory and applications," *Biosensors and Bioelectronics* 14:663 (1999); Green et al., "Surface plasmon resonance analysis of dynamic biological interactions with biomaterials," *Biomaterials* 21:1823 (2000).

One limitation of existing label-free detectors is that they tend to be significantly less sensitive than fluorescence detection. Devices such as the QCM, SPR, and microcantilever typically resolve 103 to 104 molecules per $\mu m^2$, whereas confocal flourescent microscopy can routinely resolve in the range of 1-10 molecules per $\mu m^2$.

The need for large sample volumes affects not only devices for measuring concentration, but also techniques for measuring binding energetics. The latter are also limited by the difficulty of monitoring a particular species of interest in a reaction environment. Calorimetry, for example, has been applied to thermodynamic characterization of ligand binding processes. Experiments may be performed at a constant temperature by titrating the ligand into a solution containing the binding partner in the sample cell of the calorimeter; see, e.g., Jelesarov et al., "Isothermal titration calorimetry and differential scanning calorimetry as complementary tools to investigate the energetics of biomolecular recognition," *Journal of Molecular Recognition* 12:3 (1999). After each addition of the ligand, the released or absorbed heat in the sample cell is measured relative to a reference cell filled with buffer. Both the enthalpy and binding constant can be obtained by measuring the energy change as a function of the ligand concentration. The amount of ligand consumed in an experiment may be, for example, 10-100 nmol.

Conventional calorimeters exhibit the disadvantages noted above. They typically require large sample volumes—typically in the range of 0.1 to 1 ml. In many cases, yields of the product of interest are too low to be detected within such large volumes. Calorimetry is also non-specific; the heat measured is not necessarily produced by the molecules of interest. This makes it difficult to analyze signals from complex reactions unless results from specific analytical measurements are already available.

Although several researchers have shown that microfabricated devices can detect the thermal properties of sample volumes less than a nanoliter (see, e.g., Berger et al., "Thermal analysis using a micromechanical calorimeter," *Applied Physics Letters* 69:40 (1996); Nakagawa et al., "Picojoule and submillisecond calorimetry with micromechanical probes," *Applied Physics Letters* 73:2296 (1998); Johannessen et al., "Heat conduction nanocalorimeter with p1-scale single cell measurements," *Applied Physics Letters* 80:2029 (2002)), demonstrating that microfabricated calorimeters can be highly sensitive, these devices have not yet been integrated with microfluidics.

Accordingly, there remains a need for convenient analytical techniques for accurately measuring concentrations and binding energetics, particularly in connection with small sample volumes containing diverse constituents.

DESCRIPTION OF THE INVENTION

SUMMARY OF THE INVENTION

In accordance with the present invention, free-standing microfluidic channels are used to both transport and analyze molecules of interest within small (preferably nanoliter) sample volumes. In a biochemical context, such molecules may be polypeptides, nucleic acids, or other biomolecules. More generally, however, the invention is amenable to use in connection with any molecular species susceptible to capture and binding as described below.

The free-standing channels provide a real-time readout of concentration without the need for labeling with reporter molecules. The channels can also measure enthalpy values and equilibrium constants by detecting heat released from or absorbed by the sample. Detection is accomplished by transducing the mass of adsorbed analyte molecules into changes in mechanical resonant frequency and/or by transducing the heat released from chemical reactions into bending of the channel, preferably at nanometer scales.

In one aspect, therefore, the invention comprises an apparatus for measuring at least one property relating to a chemical species of interest. The apparatus comprises one or more microfluidic channels that facilitate a chemical reaction involving a species of interest; for example, the channels may include a capture moiety for the species of interest. Reaction of the species (e.g., binding of the species to the capture moiety) imparts a physical change to the channel, which is measured by a detector in order to characterize the property or properties. For example, the property may be binding affinity for the capture moiety, or binding energy, or both.

In a preferred embodiment, the apparatus comprises a plurality of free-standing microfluidic channels that transport fluid samples and detect binding activity within small sample volumes. The channel may be operated in two modes. In one regime, molecules of interest are detected by measuring the change in channel mass as the molecules bind to the capture moiety. The mass is determined by measuring the resonant frequency of the free-standing channel. As molecules attach to the capture moieties (whose locations remain fixed within the channel), the net increase in mass decreases the resonant frequency. Molecular specificity is achieved through the use of functionalized capture moieties, e.g., proteins such as antibodies or enzymes, antigens, nucleic acids complementary to a nucleic acid under study, etc.

In the second mode of operation, the affinity and energetics of binding reactions are detected by measuring the bending of the channel in response to the reaction. In one embodiment, this is accomplished using a thermal bimorph comprising the microfluidic channel and a material (e.g., metal) on the exterior surface of the channel. A temperature change leads to unequal thermal expansion for the two layers, which causes the entire structure to bend. The magnitude of the bending corresponds to the heat transferred during the binding reaction.

It should be noted that bending can also be used to measure concentration, e.g., by asymmetrically functionalizing the interior surfaces of the channel with the capture moiety.

The free-standing microfluidic channels of the present invention offer at least three advantages over conventional approaches. First, detection is label-free and real-time. This eliminates the need for site-specific attachment of reporter molecules. Second, the thermal detection requires a sample volume that may be several orders of magnitude smaller than conventional microcalorimeters. And third, the detectors themselves are microfluidic channels. This allows the detection to be directly integrated with microfluidic systems.

In a second aspect, the invention comprises a method of measuring at least one property relating to a chemical species of interest. The method utilizes a microfluidic channel facilitating chemical reaction of the species of interest. A solution comprising the species of interest is caused to flow through the channel, and a chemical reaction involving the species imparts a physical change to the channel. This physical change is measured in order to characterize the property or properties.

BRIEF DESCRIPTION OF THE DRAWINGS

The foregoing discussion will be understood more readily from the following detailed description of the invention, when taken in conjunction with the accompanying drawings, in which.

DETAILED DESCRIPTION OF THE PREFERRED EMBODIMENTS

Figure 1:
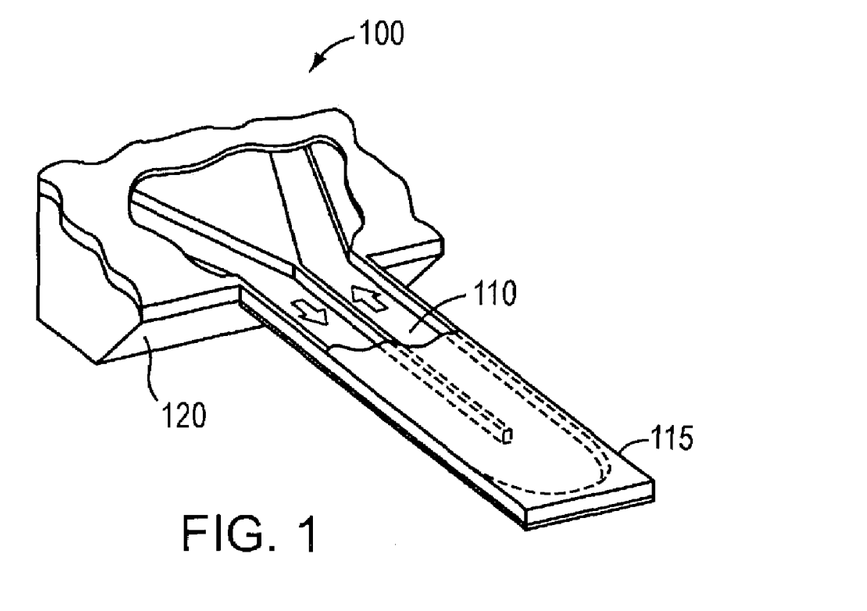
FIG. 1 is perspective view of a free-standing microfluidic channel in accordance with the present invention.

Refer first to FIG. 1, which illustrates the basic configuration of an analytical cell 100 useful in connection with the present invention. The device 100 includes a U-shaped, free-standing microfluidic channel 110 defined as a hollow within an elongated, finger-like cantilever 115 that projects from (and is integral with or joined to) a mechanically stable supporting substrate 120. Fluid flowing through a channel within the substrate enters the cantilever 115 and traverses the channel 110 as indicated by the arrows.

Figure 2:
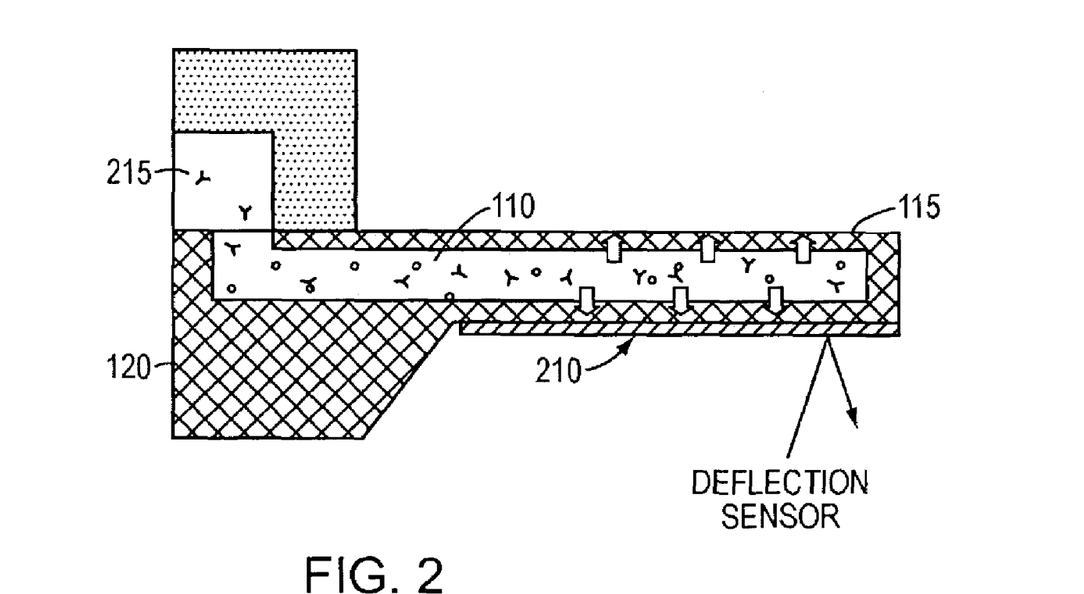
FIG. 2 is a sectional view of a microfluidic channel as shown in FIG. 1, and configured for measurement of heat released by molecules within the channel.

In one configuration, calorimetric measurements are accomplished by detecting the bending of a thermal bimorph. As shown in FIG. 2, the bimorph comprises the cantilever 115 containing a microfluidic channel 110 and a material (e.g., a metal, such as gold or aluminum) 210 that is deposited on the exterior surface of the cantilever 115. The material 210 has a coefficient of thermal expansion different from that of the cantilever 115. As a result, a temperature change leads to unequal thermal expansion, which causes the structure (i.e., the metal-treated cantilever 115) to bend.

This temperature change arises from reaction between different species within the channel 110. The different species may be free, reacting as the sample passes from a source channel 215 into and through the channel 110. Alternatively, however, one (or more) of the species may be bound within channel 110. In one embodiment, the bound species is attached to surfaces (e.g., interior walls and/or structures within the channel, as described below). In another embodiment, the bound species is suspended within a gel that fills channel 110. In each case, a potential difference may be established through the channel, and species of interest caused to circulate through the channel electrophoretically.

The bound species may be a nucleic acid, a polypeptide, a protein nucleic acid, a substrate interactive with a polypeptide (e.g., an enzyme), an enzyme interactive with a substrate, an antibody interactive with an antigen, an antigen interactive with one or more antibodies, or other biomolecule. As the reaction takes place, heat is evolved (as indicated by the arrows), affecting the material of cantilever 115 as well as external material 210. The degree of cantilever deflection, which may be measured using a deflection sensor (e.g., the optical arrangement described below), reflects the amount of heat evolved.

Figure 3A:
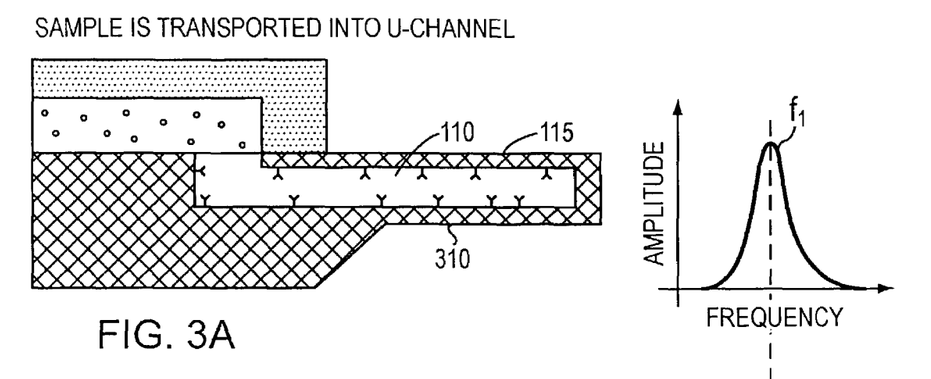
FIGS. 3A-3C are sectional views of a microfluidic channel as shown in FIG. 1, and illustrate detection of mass contributed by molecules that bind to the channel interior.
Figure 3B:
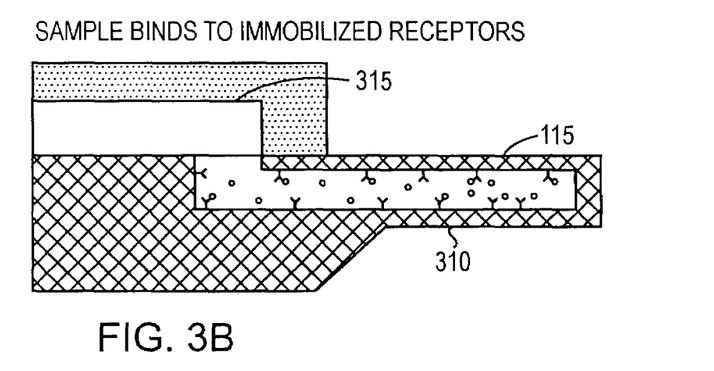
Figure 3C:
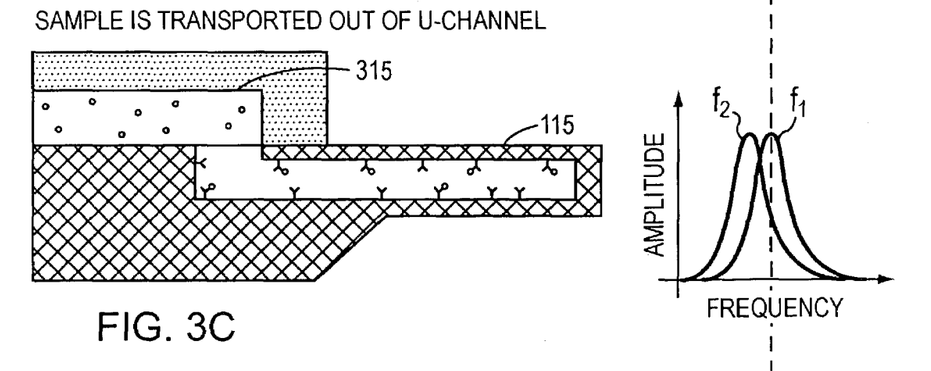

In another configuration, illustrated in FIGS. 3A-3C, the device 100 measures the extent of reaction between one or more free species and a receptor species 310 within channel 110 (again, bound to one or more interior surfaces or to a gel within the channel). As shown in FIG. 3A, a sample containing a chemical species of interest is transported into the channel 110 by, for example, electrokinetic or pressure-induced flow from a source channel 315. Prior to entry of the sample, the cantilever 115 has a mechanical resonant frequency $f_1$ as illustrated in the graph. As the sample progresses through channel 110, a portion of the species of interest binds to the immobilized receptors 315 (FIG. 3B), and the remaining, unbound sample molecules are transported out of the channel 110 (FIG. 3C). The additional mass of the bound species affects the resonant frequency of cantilever 115, decreasing it to $f_2$ as shown. The difference in frequency $f_1 - f_2$ at equilibrium will depend, in a predictable and quantitative fashion, on the total number of adsorbed molecules. This quantity, in turn, depends on the concentration.

Cantilever bending can also be used to determine the extent of reaction within the channel. Instead of using a thermal bimorph, the interior surfaces of channel 110 are asymmetrically functionalized, and bending occurs due to differential surface stresses (see, e.g., Fritz et al., "Translating Biomolecular Recognition into Nanomechanics," *Science* 288:316-318 (2000)). For example, in one embodiment, the bottom (interior) surface of channel 110 is plated with a material, such as gold, to which biomolecules may be attached using well-known chemistries; the upper surface is not plated. As a result, receptor molecules introduced within channel 110 may be caused to attach chemically to the gold-plated lower surface but not the upper surface. When the species of interest is introduced into the channel, it, in turn, binds only to the attached receptors, causing differential surface stress that results in bending of the cantilever 115.

Receptor molecules may also be preferentially attracted and bound to one interior channel surface through application of a voltage. For example, applying a potential difference across a deposited metal layer 210 and an electrolyte solution within channel 110 will alter the surface charge on the interior surface of channel 110 opposite layer 210, thereby preferentially attracting (or repelling) receptor molecules to (or from) that surface as compared with other surfaces. It should be emphasized that the unaffected surfaces need not be entirely free of receptor molecules. So long as the relative receptor population on the affected surface as compared with the population on the opposite surface is known, the degree of bending will be indicative of the extent of reaction.

The resonant frequency of cantilever 115 may readily be measured by arrangements well-characterized in the art, e.g., using the optical lever (where a laser beam is reflected from the end of the cantilever) or a laser vibrometer that utilizes a laser to illuminate the cantilever and measures the frequency response by means of Doppler shifts. See, e.g., J. Yang et al., "Mechanical behavior of ultrathin microcantilever," *Sensors and Actuators* 82:102-107 (2000) (hereafter "Yang et al."), the entire disclosure of which is hereby incorporated by reference. Alternatively, integrated detection can be achieved by piezoresistive or piezoelectric detection. Mass resolution is discussed in greater detail below.

Inserting the solution inside the cantilever 115 has appreciable advantages over the conventional approach of inserting a cantilever into a sample solution. For mass detection, the resolution is related to the cantilever geometry, its resonance quality factor Q, and the environment. In vacuum, the Q of cantilever devices may exceed $10^4$, and a mass resolution of 100 kD ($10^{-19}$ g) is theoretically obtainable. In fluid, by contrast, the resolution is dramatically reduced by viscous drag. Since a microfluidic channel is not impeded by viscous drag, and is capable of operating in vacuum without perturbing the molecules within the fluid, the mass resolution may be significantly higher than a standard cantilever. It should also be more sensitive than the quartz crystal microbalance and may potentially be comparable to fluorescence detection. For calorimetry, replacing the cantilever with a microfluidic channel (FIG. 2) allows the sample to be isolated within a well-defined volume (pL-nL scale) while also having direct access to microfluidic delivery.

Figure 3D:
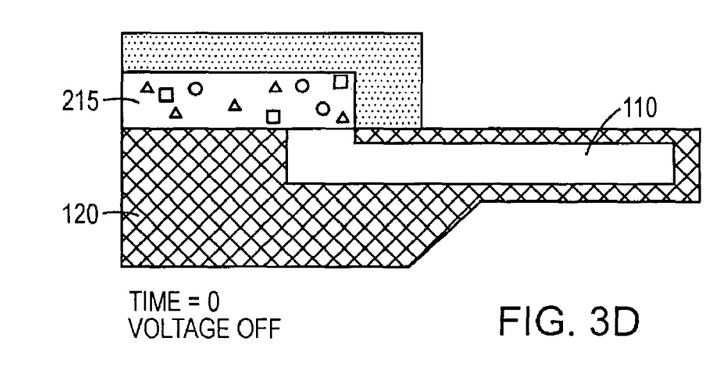
FIGS. 3D-3F are perspective and sectional views of a microfluidic channel as shown in FIG. 1 and adapted for electrophoretic movement of analyte species, e.g., to facilitate analysis of multiple species.
Figure 3E:
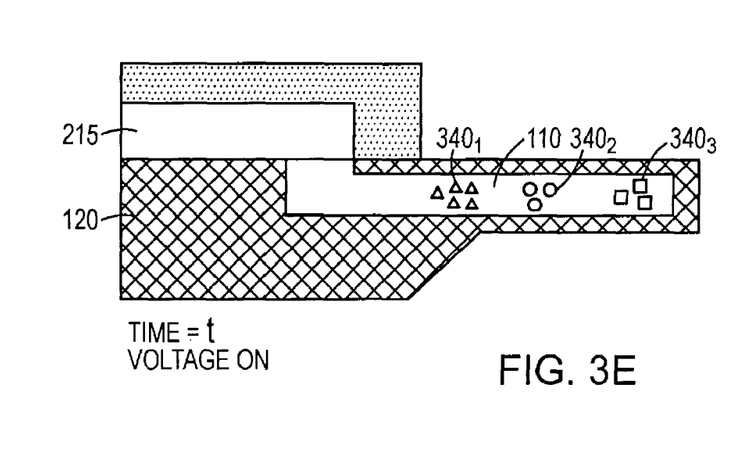
Figure 3F:
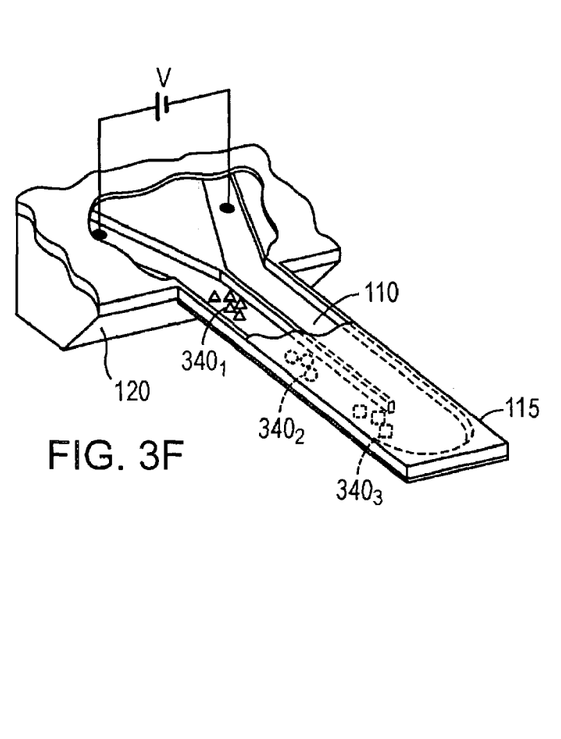

FIGS. 3D-3F illustrate use of a microchannel cantilever in accordance with the invention to separate molecules by size and/or charge. As shown in FIG. 3D, a voltage source V applies a potential difference across the length of channel 110. Three charged species of interest $340_1$, $340_2$, $340_3$ differ in terms of net charge and/or molecular weight and are initially in source channel 215 (FIG. 3D). When a voltage is applied, the species $340_1$, $340_2$, $340_3$ migrate through channel 110 at different rates, thereby separating into fractions (FIGS. 3E and 3F). Alternatively, if the species of interest $340_1$, $340_2$, $340_3$ are uncharged, they can be forced through channel 110 under pressure, and separation may occur through, for example, differential affinity binding to a bound receptor (in the manner of conventional affinity chromatography).

Traversal of the species through channel 110 can be monitored by continuously observing the resonance of cantilever 115. This approach can be used to obtain various types of information. Species concentrated at the base of cantilever 115 (i.e., at the entrance or exit of channel 110) have less of an effect on the resonant frequency than species concentrated at the tip of cantilever 115. As a result, useful information concerning the charge and/or mass of the species in channel 110 can be obtained both from the over-all resonance time profile (i.e., the change in cantilever mass over time) as the species travel through the channel, as well as peak resonance frequencies observed as different species reach the cantilever tip. For example, since a lower resonant frequency indicates a larger tip mass, comparison of the peak resonant frequencies observed for different samples can indicate differences in fraction masses, with each peak frequency effectively representing a "signature" of the species then at the cantilever tip. The speed with which the different species travel through channel 110 under the influence of a voltage, as indicated by the resonance time profile, reflects both mass and charge, while the time between peaks depends on differences in mass and/or charge among the fractions. Indeed, if the fractions are separated by a distance greater than the cantilever length, a separate resonance signature can be observed for each fraction.

Samples with different species contents can also be compared. For example, a first sample run through channel 110 may contain known concentrations of all three species, while a second sample, run subsequently through the same channel or simultaneously through an adjacent channel, may have an unknown quantity of one of the species. By comparing the resonance time profile of the second sample to that of the first (reference) sample, it is possible to determine the unknown concentration in the second sample. Moreover, even if the absolute concentrations in the first sample are not known, comparison of the resonance time profiles will indicate relative concentrations between the two samples.

Figure 4:
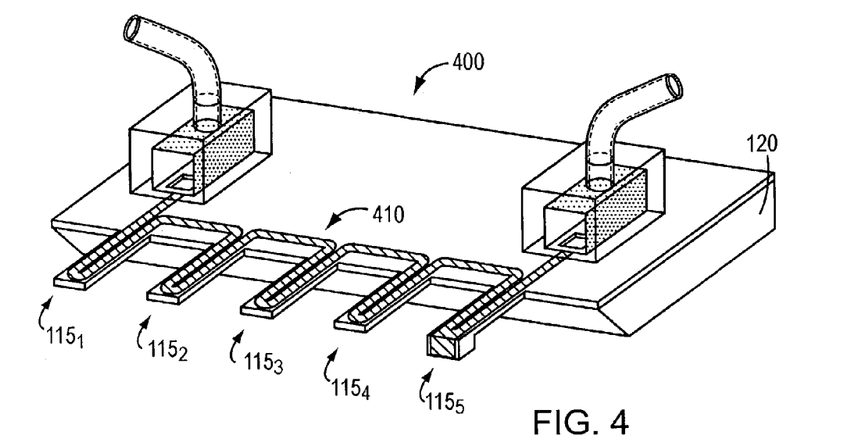
FIG. 4 is a perspective view of a system utilizing a plurality of channels, arranged in series, one of which is configured for calorimetric measurement while the others detect mass.

Since the detector itself is a microfluidic channel, multiple detectors can be connected together, as illustrated in FIG. 4. A composite device 400 includes a series array of parallel cantilevers $115_1 \ldots 115_5$ each defining U-shaped channels along a single fluid path 410. Multiple cantilevers 115 can be used to measure multiple parameters. For instance, a calorimeter $115_5$ can be integrated with multiple mass detectors that are each functionalized with different capture moieties (achieved, for example, by selectively applying light or an electric field to different cantilevers in the presence of the different capture moieties, so that a different moiety is bound within each of the channels, or by having separate fluidic paths to each cantilever). Thus, multiple parameters of and/or species within a complex mixture can be analyzed while consuming nanoliter-scale sample volumes. Moreover, the parallel cantilever configuration may be employed to facilitate detection by optical interference.

Figure 5A:
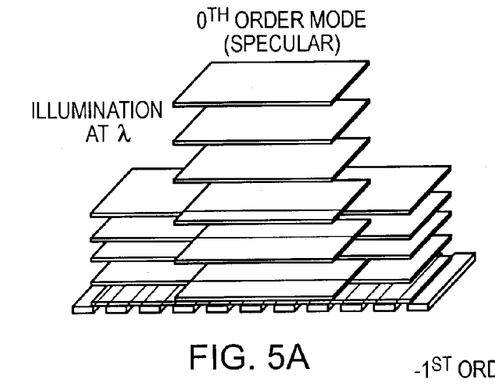
FIGS. 5A and 5B conceptually illustrate measurement of displacement of interdigitated fingers.
Figure 5B:
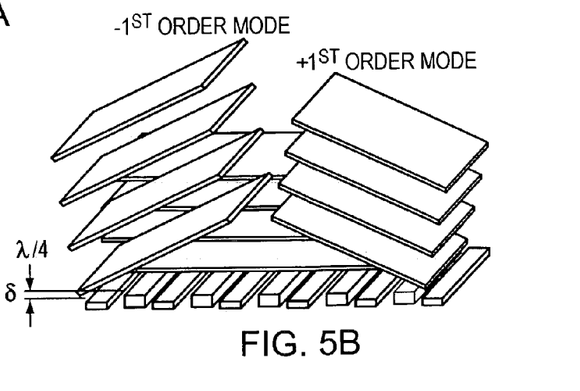

Measurement reliability is typically ensured by incorporation of a control, or reference, to which the measurement can be compared. For instance, thermal measurements are commonly acquired differentially using a reference vessel to measure heat released from a sample lacking the molecules of interest. In the present context, differential measurements can be obtained by measuring the relative bending between two adjacent cantilevers. As described in U.S. Pat. No. 6,473,187 (hereby incorporated by reference) and as shown in FIGS. 5A and 5B, when illuminated with coherent light, interdigitated fingers form a phase-sensitive diffraction grating, and the out-of-plane displacement is determined by measuring the intensity of a diffracted mode. Specifically, when the fingers are illuminated with a laser, the reflected light produces a diffraction pattern composed of several modes. The intensities of these modes depend on the relative out-of-plane distance between the interdigitated finger sets. When the two finger sets are perfectly aligned, the even numbered modes have maximum intensity, whereas the odd numbered modes are dim (see FIG. 5A, in which only $0^{th}$ mode is shown). The opposite occurs when one set is displaced by an amount δ that is an odd multiple of λ/4 of the laser wavelength. Thus, arbitrary displacements between the two sets of fingers can be determined by measuring the intensity of one of the modes. As explained in the '187 patent, intensity can be measured using a simple illumination source and a photodiode detector.

Figure 6:
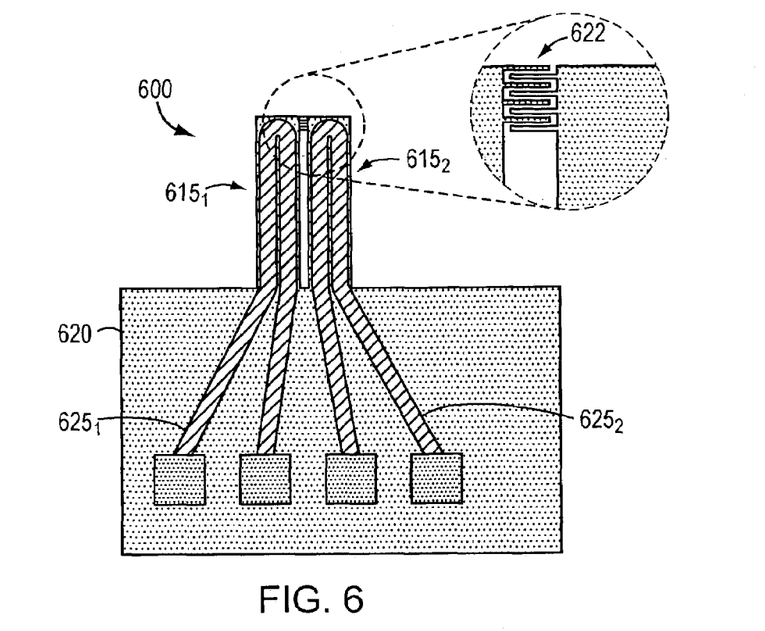
FIG. 6 is a plan view of a system configured for differential measurement based on interdigital displacement.

Measurements can be differential—that is, the relative degree of bending (and, hence, heats of reaction) caused by different chemical interactions can be measured directly. This may be accomplished, for example, by providing two or more sets of interdigitating fingers, each set projecting from adjacent cantilevers. As shown in FIG. 6, a pair of cantilevers $615_1$, $615_2$ extend from a common substrate 620. The cantilevers $615_1$, $615_2$ have complementary sets of interdigitating fingers, as indicated at 622. A separate fluid path $625_1$, $625_2$ runs through each of the cantilevers $615_1$, $615_2$, respectively. In this way, different reactants can be applied to the different cantilevers and the relative degrees of bending detected. If desired, each cantilever $615_1$, $615_2$ may also include an additional set of fingers interdigitating with fingers projecting from the substrate 620, thereby facilitating absolute measurements.

Alternatively, using the arrangement shown in FIG. 4, the interiors of different channels may be differently functionalized. The degrees of bending of the differently functionalized cantilevers may be measured relative to their immediate neighbors or relative to the substrate by diffractive-mode sensing.

Thus, for thermal measurements, two cantilevers 115 may be coated with metal on one side to create temperature-sensitive bimorphs. Temperature variations induced by external (nonspecific) sources will bend both structures equally and there will be no change in the optical signal. When energy is released from reactions in one of the cantilever channels, however, the temperature of that channel will increase and the cantilever will deflect relative to the reference cantilever. Since the material of the cantilevers (e.g., silicon nitride) can be optically transparent, it is also possible to acquire fluorescence as well as make photothermal measurements. For protein assays, the reference is established by functionalizing each channel differently. For instance, one channel can be functionalized with a receptor protein and the other can be coated with molecules that block protein binding.

The interdigital detector has at least three advantages over conventional deflection detectors such as the optical lever: (i) the readout is inherently differential, eliminating the need to electronically subtract the signals after making the measurement; (ii) the resolution may be an order of magnitude ($\sim 10^{-4}$ Å/rtHz at 1 kHz) higher than the optical lever; and (iii) the alignment requirements for the illumination source and the photodetector are reduced. The first two advantages improve the thermal and mass resolution, and the third is useful for detecting the channel resonance in vacuum.

The microfluidic channels are designed to detect the mass (rather than stress) of molecules that bind to the interior channel walls. This detection scheme has at least two important advantages. First, multiple channels can be functionalized simultaneously or in rapid succession using standard microfluidic networks. (At present, bioanalytic cantilevers are typically functionalized one at a time by manually inserting them into micropipettes.) And second, the molecular detection limit of the mass sensor will be high.

The fluidic channels can initially be filled by capillary forces or, in some cases, by applied pressure. As noted above, electrophoretic flow may be employed to introduce the biomolecules. Provided that the molecules of interest are charged, they can be continuously delivered in this fashion without disrupting the mechanical stability of the freestanding channels, thereby facilitating real-time measurements. For uncharged molecules, other conventional flow-driving techniques may be utilized.

Figure 7A:
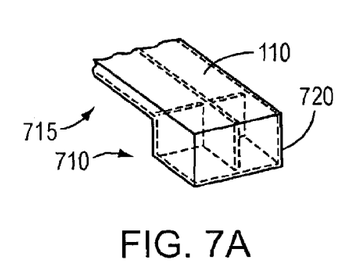
FIG. 7A is a perspective view of a sample chamber with an expanded cap volume for thermal measurements.

The time response and total released heat of the thermal measurement will depend on the sample volume in the suspended portion of the microfluidic channel. The volume of a single channel 110, however, may be less than 100 pL. One way to increase the sample volume for a given channel geometry while preserving the temperature sensitivity of the channel/metal bimorph is illustrated in FIG. 7A, in which the tip 710 of a cantilever 715 is enlarged into a sample vessel 720 (which may be internally divided into separate chambers, as shown). In this configuration, the majority of the heat released from reactions within the vessel will be conducted through the channel bimorph.

Figure 7B:
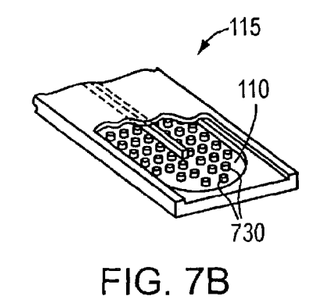
FIG. 7B illustrates the use of columns in a sample chamber to improve mechanical stability.

Another variation, illustrated in FIG. 7B, involves the placement of structural supports, such as columns 730 (which may be fabricated, e.g., from silicon nitride), throughout the interior of the channel. The columns 730 increase the mechanical stability of the channel 110 by preventing the top and bottom surfaces from making contact. They also increase the net surface area for placement of capture moieties. Arrays of columns 730 can be placed in the microchannel 110 without increasing the complexity of the fabrication process.

Mass Resolution

As noted above, one useful approach to estimating the mass resolution is described in Yang et al. According to their analysis, the resonant frequency shift of the microcantilever is $$\delta m = \frac{k}{4\pi^2}\left(\frac{1}{f_1^2} - \frac{1}{f_2^2}\right)$$

where δm is the mass to be detected, k is the spring constant, and $f_1$ and $f_2$ are the resonance frequencies of the unloaded and loaded cantilever, respectively. The minimum detectable frequency shift as determined by conventional techniques such as slope detection or frequency modulation methods is $$\delta\omega = \frac{1}{A}\sqrt{\frac{\omega_0 k_B TB}{kQ}}$$

where $k_b$ is Boltzmann's constant, A the oscillation amplitude, B the bandwidth, $\omega_0$ the resonance frequency, T the temperature, and Q the quality factor. For conventional microcantilevers, typical values for these parameters are: k=0.01–10 N/m, $\omega_0$=5–500 kHz, A=1–1000 nm, Q=1–10 (water), 100 (air), $10^4$ (vacuum), and B=1 ms–1 s. Based on the optimal choice of these values, the minimum frequency shift, $\delta\omega_0$, is about 1 MHz, corresponding to a mass resolution of $10^{-19}$ g, or 100 kDaltons. Yang et al. have demonstrated that in vacuum, a mass of ~$10^{-17}$ g can be resolved using a microcantilever with a 80 μm length, 10 μm width, and 170 nm thickness. This corresponds to a resolution on the order of $10^{-20}$ g/μm² (roughly one molecule per μm²). When the cantilever is inserted into a solution, its resonant frequency is given by $$\omega_0 = \sqrt{\frac{K}{M_e + M_I}}$$

where $M_e$ is the effective mass of the cantilever and $M_I$ is the induced mass which depends on parameters of the solution (such as viscosity and mass density). For most situations, $M_I$ is sufficiently larger than $M_e$ that the mass resolution is significantly lower. As a result, microcantilevers can be used to measure the viscosity of a solution.

Although fabrication of the microfluidic channel of the present invention will ordinarily result in a device having a spring constant and resonant frequency within the ranges stated previously, the actual Q of the structure is unknown because of the effects of the fluid inside. However, because the channel height is sufficiently thin (250-500 nm) and the Reynolds number is low due to the small length scale and high excitation frequency, the energy loss to the fluid layer should be minimal. In addition, given that the mass resolution depends on the square root of the Q, even a significant reduction need not sacrifice analytically useful resolutions. Finally, it should be noted that the mass change detected by the microfluidic channel is based on a difference between the mass densities of the biomolecules and the solution density.

Thermal Resolution

Mechanical analysis of the microfluidic channel with dimensions given in FIG. 1 reveals a temperature sensitivity of ~$10^{-3}$ K/nm. The thermal time response of the channel bimorph is roughly 1 ms. Since the thermal conductivity of water is six times less than that of silicon nitride, and the water thickness is comparable to that of the nitride, the thermal sensitivity should also be ~10 nJ.

The utility of the thermal measurement will depend on the minimal sample volume that is required to fill and prime the microfluidic channels. Assuming a conservative estimate of 1 μL for the total sample volume, 1 nL for the channel+vessel volume, 10 nmol of sample, and 10 nJ resolution, it should be possible to detect a thermal change of 1 kJ/mol. For comparison, the enthalpy for the hybridization of a 16 bp DNA duplex is 436 kJ/mol. Preparing the sample within adjacent microfluidics will substantially reduce the amount of sample required.

Microfluidic networks adjacent to the free-standing channels can be designed to control the ligand concentration for titration measurements. This can be accomplished by using the laminar flow associated with microfluidics to transport multiple reactants into a given channel. Once the flow is stopped, the reactants will mix by diffusion and the released heat can be measured.

Fabrication

The structures described herein may be fabricated using conventional silicon-processing techniques. Each process run may, for example, utilize several six-inch silicon wafers, enabling fabrication of several hundred independent devices in a single run.

Figure 8A:
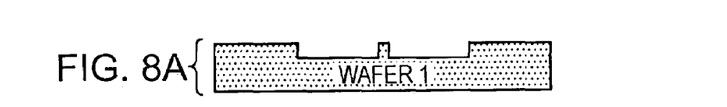
FIGS. 8A-8E illustrate a fabrication process flow.
Figure 8B:
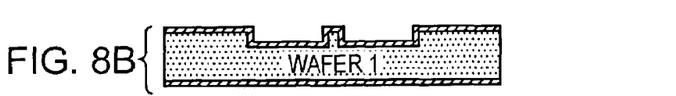
Figure 8C:
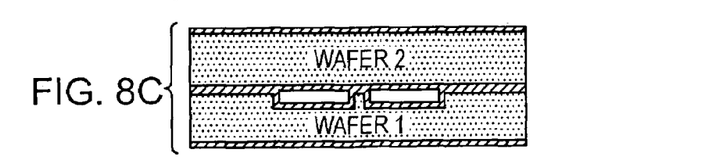
Figure 8D:
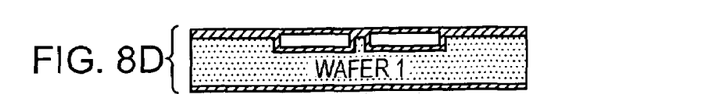
Figure 8E:
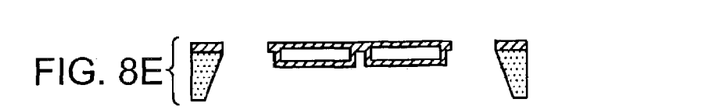

Device fabrication begins by defining the channels in silicon with a reactive ion etcher (RIE) as shown in FIG. 8A. Next, low-stress silicon nitride is deposited on wafer 1 (FIG. 8B). This wafer is then bonded to a second wafer (wafer 2) which is also coated with silicon nitride (FIG. 8C). The top nitride layer of wafer 2 is dry-etched away, and all of the exposed silicon is removed with potassium hydroxide (KOH) (FIG. 8D). The 'U' shape and channel openings are etched into the nitride by RIE and the silicon wafer is etched in KOH such that U-channels overhang from a silicon die (FIG. 8E). Finally, PDMS microfluidic channels are attached to the top side to create macroscopic fluidic connections. The dimension of the U-channels may be, for example, 250-500 nm nitride thickness, 500 nm channel height, 200-500 μm length, and 50-100 μm width.

There are three aspects of this process which involve straightforward but specialized microfabrication techniques. (i) Releasing free-standing nitride structures requires the front and back sides of the wafer to be patterned such that after a long etch in KOH, individual devices with intact structures can readily be separated from the wafer. (ii) Molded PDMS microfluidic channels are aligned and sealed to the nitride channels in order to connect them to macroscopic fluidics. A representative procedure for this process is described in Duffy et al., "Rapid prototyping of microfluidic systems in poly(dimethylsiloxane)," *Analytical Chemistry* 70:4974 (1998), which is hereby incorporated by reference. (iii) Wafers coated in silicon nitride are bonded together. While wafer bonding with silicon dioxide is common practice, bonding with silicon nitride is less common. One useful technique involves chemical mechanical polishing (CMP) of the nitride in order to reduce the surface roughness from over 10 nm to less that 1 nm, which generally ensures successful bonding.

Having described certain preferred and exemplary embodiments of the invention, it will be apparent to those of ordinary skill in the art that other embodiments incorporating the concepts disclosed herein can be used without departing from the spirit and the scope of the invention. The described embodiments are to be considered in all respects only as illustrative and not limiting. Therefore, it is intended that the scope of the present invention be only limited by the following claims.

What is claimed is:

1. A method of measuring at least one property relating to a chemical species of interest, the method comprising the steps of:
   a. providing an enclosed microfluidic channel formed by a hollow in an elongated projection that projects from a substrate to which the projection is fixed at one end;
   b. flowing a fluid containing the species of interest through the channel to cause therein binding between the species of interest and at least a second chemical species, the binding being related to the at least one property and imparting a physical change to the channel, wherein the physical change is bending of the entire channel; and
   c. measuring the physical change to characterize the at least one property.

2. The method of claim 1 wherein the second chemical species is a capture moiety.

3. The method of claim 2 wherein the channel comprises an interior surface to which the capture moiety is bound.

4. The method of claim 2 wherein the capture moiety is contained in a gel within the channel.

5. The method of claim 2 wherein the capture moiety is not bound within the channel.

6. The method of claim 1 wherein the property is concentration of the species of interest.

7. The method of claim 1 wherein the property is binding energy between the species of interest and the second chemical species.

8. The method of claim 7 wherein the channel comprises a thermal bimorph, the bending resulting from differential thermal expansion and indicating heat released by binding.

9. The method of claim 1 wherein the second chemical species is non-uniformly active within the channel, the bending resulting from differential surface stresses.

10. The method of claim 1 wherein the bending is detected optically.

11. A method of measuring concentration of a chemical species of interest, the method comprising the steps of:
    a. providing an enclosed microfluidic channel formed by a hollow in an elongated projection that projects from a substrate to which the projection is fixed at one end;
    b. flowing a fluid containing the species of interest through the channel to cause therein binding between the species of interest and at least one capture moiety bound to an interior surface of the channel or contained in a gel within the channel; the binding being related to the concentration of the species of interest and imparting a physical change to the channel, wherein the channel has a mechanical resonant frequency and the physical change is alteration of the mechanical resonant frequency of the channel in relation to a mass of the species of interest; and
    c. measuring the physical change to characterize the concentration of the species of interest.

* * * * *